United States Patent
Fuchs et al.

(10) Patent No.: US 6,795,198 B1
(45) Date of Patent: Sep. 21, 2004

(54) METHOD AND DEVICE FOR MEASURING THIN FILMS AND SEMICONDUCTOR SUBSTRATES USING REFLECTION MODE GEOMETRY

(76) Inventors: Martin Fuchs, 11 Sophia Dr., Uxbridge, MA (US) 01569; Matthew J. Banet, Two Union Park, No. 4, Boston, MA (US) 02118; Keith A. Nelson, 55 Clearwater Rd., Newton, MA (US) 02162; John A. Rogers, 7412 Berkeley Cir., Castle Rock, CO (US) 80104

( * ) Notice: Subject to any disclaimer, the term of this patent is extended or adjusted under 35 U.S.C. 154(b) by 747 days.

(21) Appl. No.: 09/087,141
(22) Filed: May 28, 1998

(51) Int. Cl.$^7$ ................................................. G01B 9/02
(52) U.S. Cl. .................................................... 356/521
(58) Field of Search ............................... 356/521, 432, 356/321, 318, 357; 73/655, 657, 800

(56) References Cited

U.S. PATENT DOCUMENTS

| | | |
|---|---|---|
| 3,462,223 A | 8/1969 | Tiemann et al. |
| 4,522,510 A | 6/1985 | Rosencwaig et al. |
| 4,655,547 A | 4/1987 | Heritage et al. |
| 4,710,030 A | 12/1987 | Tauc et al. |
| 4,728,165 A | 3/1988 | Powell |
| 4,812,036 A | 3/1989 | Inoue |
| 4,939,368 A | 7/1990 | Brown |
| 5,062,693 A | 11/1991 | Beratan et al. |
| 5,132,824 A | 7/1992 | Patel et al. |
| 5,220,403 A | 6/1993 | Batchelder et al. |
| 5,263,039 A | 11/1993 | Skupsky et al. |
| 5,285,438 A | 2/1994 | Marchand et al. |
| 5,344,236 A | 9/1994 | Fishman |
| 5,361,638 A | 11/1994 | Pettersson et al. |
| 5,394,413 A * | 2/1995 | Zayhowski ................... 372/10 |
| 5,438,879 A | 8/1995 | Reda |
| 5,479,256 A | 12/1995 | Tamai et al. |
| 5,546,811 A | 8/1996 | Rogers et al. |
| 5,633,711 A | 5/1997 | Nelson et al. |
| 5,672,830 A | 9/1997 | Rogers et al. |
| 5,734,470 A | 3/1998 | Rogers et al. |
| 5,812,261 A * | 9/1998 | Nelson et al. ............... 356/318 |

FOREIGN PATENT DOCUMENTS

| | | |
|---|---|---|
| WO | WO9803044 | 1/1998 |
| WO | WO9900639 | 1/1999 |
| WO | WO9900640 | 1/1999 |
| WO | WO9900641 | 1/1999 |

OTHER PUBLICATIONS

Allen et al., "Microfabricated Structures for the in situ Measurement of Residual Stress, Young's Modulus, and Ultimate Strain of Thin Films", Appl. Phys. Lett., 51:241–243, 1987.

(List continued on next page.)

*Primary Examiner*—Samuel A. Turner (57) ABSTRACT

The invention provides both a method and apparatus that measures a property of a structure that includes at least one layer. The apparatus features a laser (e.g., a microchip laser, described below) that generates an optical pulse, and a diffractive mask that receives the optical pulse and diffracts it to generate at least two excitation pulses. An optical system, (e.g., an achromat lens pair) receives the optical pulses and spatially and temporally overlaps them on or in the structure to form an excitation pattern that launches an acoustic wave. The acoustic wave modulates a property of the structure, e.g., it generates a time-dependent "surface ripple" or modulates an optical property such as the sample's refractive index or absorption coefficient. Surface ripple is defined as a time-dependent change in the morphology of the surface; its peak-to-null amplitude is typically a few angstroms or less. The apparatus also includes a light source that produces a probe beam that reflects off the modulated property to generate a signal beam. An optical detection system receives the reflected signal beam and in response generates a light-induced electrical signal. An analyzer analyzes the signal to measure the property of the structure.

35 Claims, 7 Drawing Sheets

OTHER PUBLICATIONS

Bauer et al., "Determination of the Stresses and Properties of Polymer Coatings", J. of Coatings Technology, 60:51–55, 1988.

Coburn et al., "Stress in Polyimide Coatings", J. of Polymer Science: Part B: Polymer Physics, 32:1271–1283, 1994.

Duggal et al., "Resolution of Conflicting Descriptions of Propylene Glycol Relaxation Dynamics Through Impulsive Stimulated Scattering Experiments", Polymer Communications, 32:356–360, 1991.

Duggal et al., "Real–Time Optical Characterization of Surface Acoustic Modes of Polymide Thin–Film Coatings", J. Appl. Phys. 72:2823–2839, 1992.

Fishman et al., "Surface Selectivity in Holographic Transient Grating–Diffraction", Stanford University, Stanford, CA; W.W. Hansen Exp. Phys. Lab. & Dept. of Chemistry.

Goldsmith et al., "Measurement of Stresses Generated to Cured Polyimide Films", J. Vac. Sci. Technol. 1:407–409, 1983.

Head et al., "Determination of Shear Stress at a Solder Paste/Stencil Interface", Mat. Res. Soc. Symp. Proc. 323:425–433, 1994.

Maden et al., "Stress Analysis of Thin Polyimide Films Using Holographic Interferometry", Experimental Mechanics 31:179–184, 1991.

Rogers et al., "Study of Lamb Acoustic Waveguide Modes in Unsupported Polyimide Thin Films Using Real–Time Impulsive Stimulated Thermal Scattering", J. Appl. Phys. 75:1534–1556, 1994.

Rogers et al., "Real–Time In Situ Characterization of Thin Films", Chemf. 8, 27 (1992), pp. 4–8.

Duggal, "Picosecond–Microsecond Structural Relaxation Dynamics in Polypropelyne Glycol", Journal of Chemical Physics, No. 94, pp. 7677–7688, Jun. 15, 1991.

Whitman et al., Appl. Optics, 8, 1567 (1969).

Nizzoli et al., Dynamical Properties of Solids (ed. G.K. Horton et al., North–Holland Amsterdam, 1990) vol. 6, 283.

Bortolani et al., J. Phys. C., 16, 1757 (1983).

Fishman I.M. et al., "Surface Selectivity in Four–Wave Mixing: Transient Gratings as a Theoretical and Experimental Example", J. Opt. Soc. Am. B., vol. 8, No. 9, Sep. 1991, pp. 1880–1888.

Barish et al., "Photoinduced Ionization of Bovine Serum Albumin by Holographic Relaxation Methods", J. Chem. Phys. 85:4194–4195, 1986.

Burzynski et al., "Study of Anisotrophy of Acoustic Wave Propagation in Stretched poly(vinylidene difluoride) Film Using the Picosecond Transient Grating Technique", Polymer, 30:1247–1250, 1989.

Deeg et al., "New Grating Experiments in the Study of Irreversible Photochemical Reactions", IEEE J. Quantum Electronics, QE–22:1476–1481, 1986.

Espinet et al., "Laser–induced Gratings in Nematic/Cholesteric Mixtures", App. Phys. Letters, 50:1924–1926, 1987.

Meth et al., "Experimental and Theoretical Analysis of Transient Grating Generation and Detection of Acoustic Waveguide Modes in Ultrathin Solids", J. App. Phys. 67:3362–3377, 1990.

Greene et al., Picosecond Relaxation Dynamics in Polydiacetylene–pTs, Chem. Phys. Letters, 139:381–385, 1987.

Meth et al., "Generation and Detection of Acoustic Waveguide Modes in Ultrathin Crystals Using the Transient Grating Technique", Chem. Phys. Letters, 162:306–312, 1989.

Nelson et al., "Optical Generation of Tunable Ultrasonic Waves", J. App. Phys., 53:1144–1149, 1982.

Nizzoli, "Problems with the Determination of Elastic Constants from Higher–Order Surface Waves: Results for Al on NaCl", Physical Review B, 37:1007–1010, 1988.

Noll et al., "Picosecond Photoinduced Index Changes in a Si:H and Related Alloys Measured by Transient Grating Experiments", J. Non–Crystalline Solids, 97 & 98:141–144, 1987.

Portella et al., "Four–Wave Mixing Experiments in Cresyl Violet Thin Films: Inadequacy of a Two–Level Interpretation", J. Phys. Chem., 91:3715–3719, 1987.

Prasad, "Non–Linear Optical Effects in Thin Organic Polymeric Films", Thin Solid Films, 152:275–294, 1987.

Rao et al., "Third Order Nonlinear Optical Interactions in Thin Films by Poly–p–phenylenebenzobisthiazole Polymer Investigated by Picosecond and Subpicosend Degenerate Four Wave Mixing", App. Phys. Letters, 48:1187–1189, 1986.

Rao et al., "Picosecond Transient Grating Studies of Polymeric Thin Films", App. Phys. Letters, 48:387–389, 1986.

Rose et al., Picosecond Transient Grating Transport in Anthracene Single Crystals, Measurements of Singlet Excitation, Chem. Phys. Letters, 106:13–19, 1984.

Rao et al., "Picosecond Laser–Induced Transient Grating Probe of the Mechanical Properties of High–Modulus Poly(p–phenylenebenzobisoxazole–2.6–diyl)", Macromolecules, 22:985–989, 1989.

Rothenhausler, "Plasmon Surface Polariton Fields for the Characterization of Thin Films", Thin Solid Films, 159:323–330, 1988.

A.R. Duggal et al., "Real–time Characterization of Acoustic Modes of Polyimide Thin–Film Coatings Using Impulsive Stimulated Thermal Scattering", App. Phys. Lett., 60(6) Feb. 10, 1992, pp. 692–694.

* cited by examiner

METHOD AND DEVICE FOR MEASURING THIN FILMS AND SEMICONDUCTOR SUBSTRATES USING REFLECTION MODE GEOMETRY

BACKGROUND OF THE INVENTION

This invention relates to a method and apparatus for measuring properties (e.g., thickness) of thin layers (e.g., metal films) contained in a structure.

During fabrication of microelectronic devices, thin films of metals and metal alloys are deposited on silicon wafers and used as electrical conductors, adhesion-promoting layers, and diffusion barriers. Microprocessors, for example, use metal films of copper, tungsten, and aluminum as electrical conductors and interconnects; titanium and tantalum as adhesion-promoting layers; and titanium:nitride and tantalum:nitride as diffusion barriers. Thickness variations in these films can modify their electrical and mechanical properties, thereby affecting the performance of the microprocessor. The target thickness values of metal films vary on their function: conductors and interconnects are typically 3000–10000 angstroms thick, while adhesion-promoting and diffusion-barrier layers are typically between 100–500 angstroms thick.

During fabrication of the microprocessor, films are deposited to have a thickness of within a few percent of their target value. Because of these rigid tolerances, film thickness is often measured as a quality-control parameter during and/or after the microprocessor's fabrication. Noncontact, nondestructive measurement techniques (e.g., optical techniques) are preferred because they can measure patterned "product" samples, rather than "monitor" samples. Measurement of product samples accurately indicates errors in fabrication processes and additionally reduces costs associated with monitor samples.

Optical methods for measuring thin, opaque films have been described. For example, U.S. Pat. No. 5,633,711 (entitled MEASUREMENT OF MATERIAL PROPERTIES WITH OPTICALLY INDUCED PHONONS), U.S. Pat. No. 5,546,811 (entitle OPTICAL MEASUREMENT OF STRESS IN THIN FILM SAMPLES), U.S. Pat. No. 5,672,330 (entitled MEASURING ANISOTROPIC MATERIALS IN THIN FILMS), and U.S. Ser. No. 08/783,046 (entitled METHOD AND DEVICE FOR MEASURING THE THICKNESS OF OPAQUE AND TRANSPARENT FILMS) describe an optical measurement technique called impulsive stimulated thermal scattering ("ISTS"). In ISTS two optical pulses are overlapped on a sample to form a spatially and temporally varying excitation pattern that launches counter-propagating acoustic waves. These patents and applications have the same inventors as this application, and are incorporated herein by reference. U.S. Pat. No. 5,394,413 (entitled PASSIVELY Q-SWITCHED PICOSECOND MICROLASERS) describes a small-scale "microlaser" that can be used to form the excitation pulses. U.S. Pat. No. 5,734,470 (entitled DEVICE AND METHOD FOR TIME-RESOLVED OPTICAL MEASUREMENTS) describes how a single pulse passes through a diffractive mask, e.g. a phase mask, to form the two optical pulses. These patents are also incorporated herein by reference.

In ISTS the acoustic waves a "transient grating" that includes an alternating series of peaks and nulls. A probe pulse irradiates the grating, and is diffracted to form a pair of signal beams. One or both of the signal beams are detected and analyzed to measure a property of the sample.

In another embodiment of ISTS, the two excitation beams are separated from a single beam by a partially reflecting mirror (e.g., a beamsplitter) and used to form the transient grating. The probe beam is then focused on a peak or null of the grating, where it is reflected, detected, and analyzed to determine a property of the sample; in this case the diffracted beam is not detected. Accuracy in this measurement requires the phase of the grating to be fixed, i.e., the position of the peaks and nulls must be stationary relative to the probe beam. The peaks and nulls are typically separated by a few microns, and thus even small fluctuations of the laser beam causes these components to move relative to the probe beam; over short periods of time this averages out any modulation (e.g., signal) mapped onto the probe beam. Since beams generated by conventional lasers typically undergo spatial fluctuations, active stabilization systems including optical detectors, closed-loop feedback systems, and electrooptic light modulators (or similar means) are typically used in the measurement. Such systems fix the position of the peaks and nulls, making it possible to accurately measure the reflected beam.

U.S. Pat. No. 4,522,510 describes another optical technique wherein a single excitation beam irradiates a sample and is absorbed to initiate a "thermal wave". A probe beam reflects off the thermal wave and is analyzed to determine a property (e.g., concentration of implanted ions) of the sample.

SUMMARY OF THE INVENTION

In general, in one aspect, the invention provides both a method and apparatus that when used a "reflection mode" geometry measure a property of a structure that includes at least one layer. The apparatus features a laser (e.g., a microchip laser, described below) that generates an optical pulse, and a diffractive element that receives the optical pulse and diffracts it to generate at least two excitation pulses. An optical system, (e.g., an achromat lens pair) receives the optical pulses and spatially and temporally overlaps them on or in the structure to form an excitation pattern that launches an acoustic wave (or an electronic response, or a thermal response). The acoustic wave modulates a property of the structure, e.g., it generates a time-dependent "surface ripple" or modulates an optical property such as the sample's refractive index or absorption coefficient. Surface ripple is defined as a time-dependent change in the morphology of the surface; its peak-to-null amplitude is typically a few angstroms or less. The apparatus also includes a light source that produces a probe beam that reflects off an area of the structure containing the modulated property to generate a signal beam. An optical detection system receives the reflected signal beam and in response generates a light-induced electrical signal. An analyzer analyzes the signal to measure the property of the structure.

In embodiments, the diffractive element is a phase mask that includes an optically transparent substrate (e.g., a quartz plate or microscope slide). The substrate typically features one or more patterns characterized by a series of parallel trenches having a spatial periodicity of between 0.1 and 100 microns.

As described above, the laser is typically a microchip laser that is diode-pumped and passively Q-switched. For example, the laser can include Nd:YAG, titanium:sapphire, chromium:LISAF, analogs of these materials, or a fiber laser. In typical embodiments the laser features a Nd:YAG layer having a thickness of less than 5 mm. The laser used in the apparatus emits a pulse having a duration that is typically 1 nanosecond or less.

The acoustic waves typically modulate a structure's surface. When the acoustic waves generate a time-dependent ripple on the surface the probe beam is aligned to deflect off the ripple to form the signal beam. In this case, the optical detection system includes a detector (e.g., a bi-cell detector or photodiode, described below) that generates an electrical signal that changes with a deflection angle of the probe beam. Alternatively, the modulated property is an optical property of the structure, such as a refractive index or absorption coefficient. Here, the probe beam reflects off an area of the structure containing the modulated optical property, and the optical detection system is configured to detect a phase of the reflected signal beam. Here, the optical detection system includes an interferometer.

In other embodiments, the optical system includes at least one lens that collects and overlaps the excitation pulses on or in the structure. For example, the optical system can include a lens pair (e.g., an achromat pair) having a magnification ratio of about 1:1. "About 1:1" means between 0.8:1 and 1.2:1. The apparatus also typically includes a lens that focuses the probe laser beam onto the acoustic waves. For example, when the acoustic waves generate a time-dependent ripple morphology, the probe beam irradiates a peak, null, a region between a peak or null, or a portion thereof. The probe beam can also irradiate a region of the sample undergoing a time-dependent change in refractive index or absorption coefficient.

The analyzer is configured to determine a frequency or phase velocity of the acoustic waves. These parameters can be used to determine a thickness of one or more layers in the structure. For example, the analyzer can be configured to calculate a thickness of the layer by analyzing the frequency or phase velocity, a density of the layer, and a wavelength of the excitation pattern. In other embodiments, the analyzer is configured to determine the density, resistivity, adhesion, delamination, elasticity, roughness, or reflectivity of the structure. Details of this calculation are included in the above-described patents and patent applications previously incorporated herein by reference.

The structure typically includes a silicon wafer, and the layer is a metal film composed of aluminum, tungsten, copper, titanium, tantalum, titanium:nitride, tantalum:nitride, gold, silver, platinum, or alloys thereof.

In another aspect, the apparatus features a passively Q-switched laser chat generates an optical pulse, and a photodiode that receives a portion of the optical pulse to generate a trigger pulse. The other components of the apparatus are similar to those described above. In this case, the apparatus includes a data-acquisition system that receives a light-induced electrical signal (from, e.g., a photodetector) and the trigger pulse. In response, the system generates a data signal (e.g., a signal waveform, described below) that is analyzed to measure a thickness of the layer in the structure.

In another aspect, the apparatus described above measures a property from a structure that does not contain a thin film. For example, the structure can be a semiconductor, such as an ion-implanted silicon wafer. The property can be an energy or concentration ion the ions implanted in the wafer.

Both the method and apparatus described above have many advantages. For example, these inventions use an all-optical measurement technique that effectively measures the thickness of thin films in multilayer structures without having to contact the sample. The thickness values can then be used to control a fabrication process (e.g., fabrication of a microelectronic device). The apparatus features all the advantages of optical metrology: each measurements is noncontact, rapid (typically less than 2), remote (the optical system can be as far as 10 cm from the sample), and can be made over a small region (as small as about 20 microns). Data collected in this way are analyzed to determine, e.g., film thickness with an accuracy and repeatability of a few angstroms.

Data collected in the reflection-mode geometry are optimized when the peaks and nulls of the grating are stationary relative to the focused probe beam. Two primary components for stabilizing the grating are described below: i) a diffractive mask that images the grating onto the sample is used in place of a partially reflecting optic (e.g., a beamsplitter); and ii) a small-scale microchip laser that generates a spatially stable beam is used in place of a conventional laser. These components, taken alone or combined, increase the signal-to-noise ratio of data collected in the reflection mode. This, in turn, improves the precision and accuracy to which a sample is measured.

Use of diffractive optics (e.g., a phase mask) in the optical system has particular advantages, especially when the reflected probe beam is measured and then analyzed to determine film thickness. In this embodiment, the probe beam is typically focused to a spot that is smaller than the width of a peaks and nulls in the optically induced grating. For example, the spot can be located on a grating peak, a grating null, or and area between neighboring peaks and nulls. The sample reflects or transmits the probe beam, which is then measured to determine: i) beam deflection; ii) a change in reflectivity or transmittivity due to the acoustic waves or other light-induced process; and/or iii) the optical phase or amplitude of the reflected or transmitted beam.

A pattern of a diffractive mask is imaged onto the sample to form the excitation pattern. This means that the peaks and nulls of the transient grating are spatially stabilized over long periods of time, even despite spatial fluctuations in the position or direction of the laser beam that irradiates diffracting mask. No closed-loop feedback system to stabilize the grating's phase is required. The degree to which the probe beam is modulated can be optimized by moving the probe beam across the grating pattern or by translating the diffracting mask to a pattern that moves the position of the peaks and nulls.

In addition, pulses separated by a phase mask produce significantly stronger signal beams compared to those generated by pulses separated by conventional beam-splitting methods relying on beamsplitters. This is because pulses leaving the phase mask have parallel "phase fronts", while pulses separated by a partially reflecting mirror have angled phase fronts. When overlapped in a sample, the parallel phase fronts produce many more light regions than the angle phase fronts. This decreases the damping of the acoustic waves, thereby increasing the precision to which it can be measured. This advantage is described in more detail in U.S. Ser. No. 09/086,975 (entitled METHOD AND DEVICE FOR MEASURING THE THICKNESS OF THIN FILMS IN MULTILAYER STRUCTURES, filed on the same day as the present application), the contents of which are incorporated herein by reference.

Use of a small-scale microchip laser in the reflection-mode geometry also minimizes spatial fluctuations of the grating, thereby increasing the quality of the measured data. This is because the beam emitted from the microchip laser undergoes very small spatial fluctuations, presumably due to the laser's compact geometry. A typical microchip lasers features thin layers of a gain media (typically Nd:YAG)

bonded to a saturable absorber (typically $Cr^{+4}YAG$) The total size of this structure is typically less than 1 $mm^3$. During operation, the microchip laser is pumped by an external diode laser. Because of its small size, the microchip laser is heated uniformly during the pumping process and requires only air cooling. These factors significantly reduce the amount of "Pointing instabilities" (i.e. spatial beam fluctuations) typically present in larger lasers. This results in a very stable beam that has basically no spatial jitter, and consequently increases the spatial stability of the excitation pattern. Another advantage is that use of a diffractive mask and an imaging system minimizes the number of optical elements (e.g., mirrors, beamsplitters) required to form an excitation pattern on a sample's surface. Only a single lens pair is needed. This simple optical system potentially reduces spatial fluctuations between the excitation pattern and the probing area caused by other optics (e.g., mirrors and beamsplitters), thereby allowing signal waveforms having high signal-to-noise ratios to be acquired.

Other features, aspects, and advantages of the invention follow from the following detailed description, and from the claims.

DETAILED DESCRIPTION

Figure 1A:
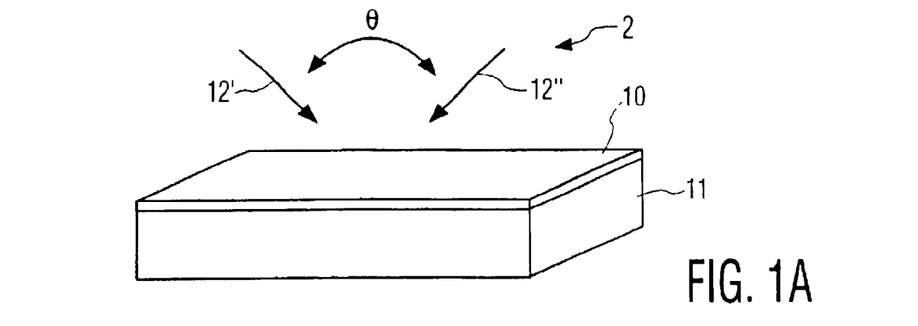
FIGS. 1A–1D show, respectively, top views of a structure being measured in a "reflection-mode" geometry according to the invention prior to irradiation with an excitation pattern; during irradiation with the excitation pattern; when a time-dependent ripple is present on the structure's surface; and when the ripple is not present on the structure's surface.
Figure 1B:
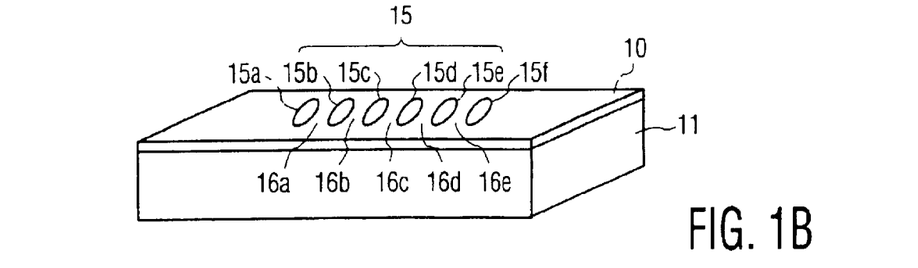
Figure 1C:
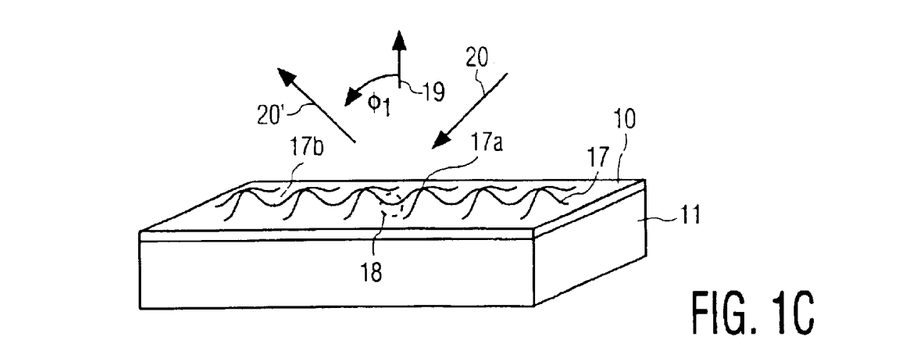
Figure 4:
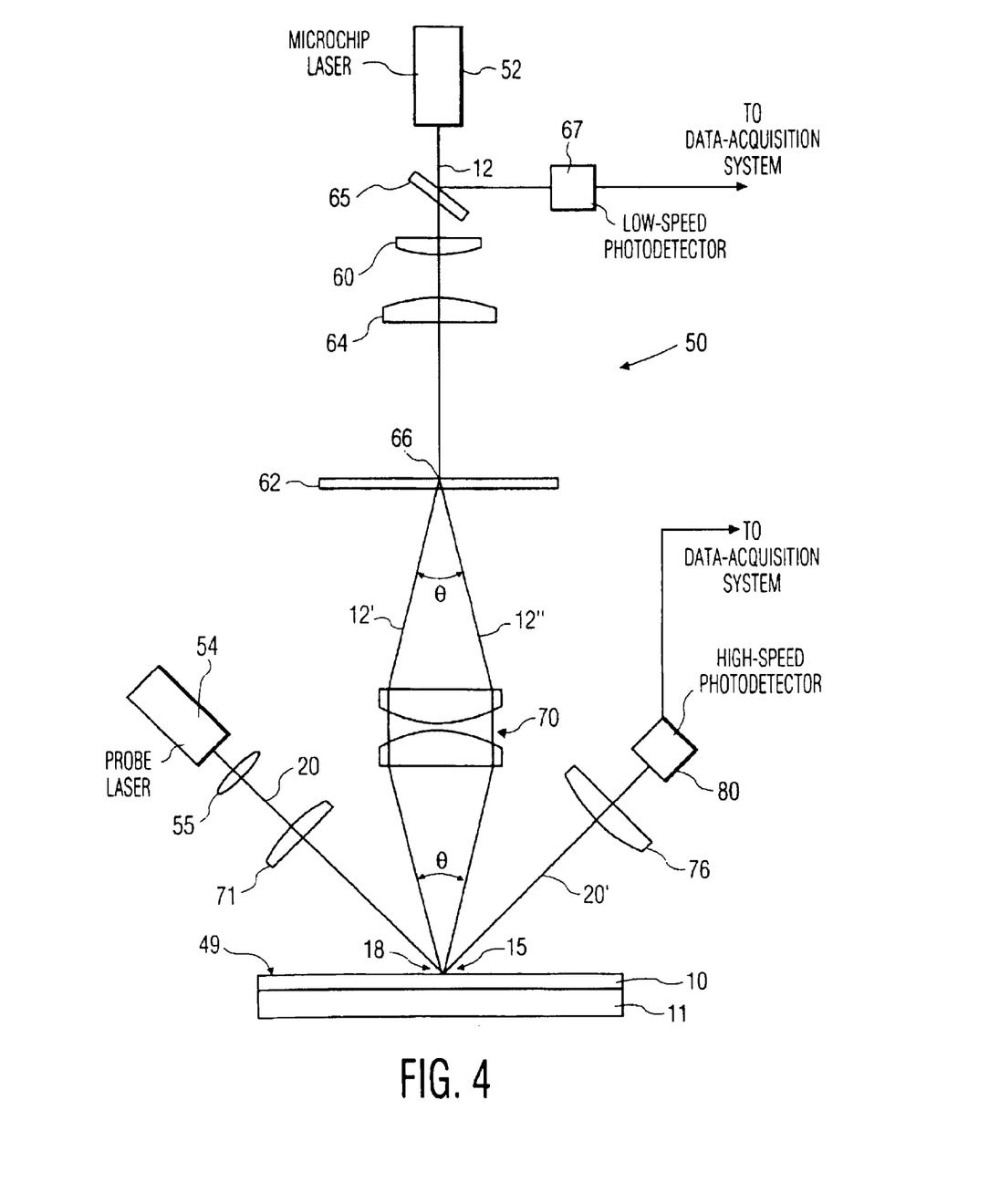
FIG. 4 shows a schematic, cross-sectional view of an optical system according to the invention.

FIGS. 1A–1C and FIG. 4 show a measurement method 2 and optical system 50 according to the invention wherein excitation 12', 12" laser pulses and a probe 20 laser beam configured in a reflection-mode geometry measure a thin film 10 disposed on a substrate 11 FIG. 4 shows how an excitation laser pulse 12 from a microchip laser 52 irradiates a phase mask 66 to generate the excitation pulses 12', 12'". The method 2 and system 50 determine, e.g., the film's thickness. The pulses 12', 12" converge on the sample at an angle θ and are overlapped and optically interfere to form a spatially periodic excitation pattern 15. The pattern 15 features alternating light regions 15a–f and dark regions 16a–e that occur at a spatial wavelength of about 0.1 and 100 microns. The film 10 absorbs radiation in the light regions 15a–f and in response thermally expands to launch counter-propagating acoustic waves through ISTS. The acoustic waves modulate a property of the film in a spatially periodic, time-dependent pattern that matches the wavelength of the excitation pattern 15. In FIG. 1C the acoustic waves modulate the film's surface to form a spatially periodic, time-dependent ripple 17 that includes alternating peaks 17a and nulls 17b. These features undulate up and down at a frequency that depends on: i) the wavelength of the excitation pattern; ii) the thickness of the film; and iii) the density and sound velocity of the film.

Figure 1D:
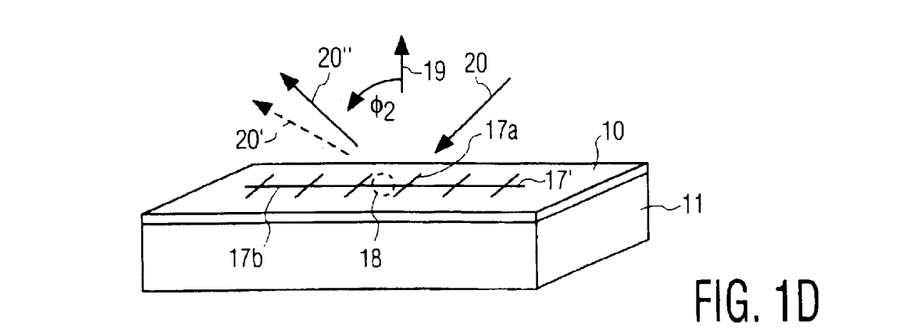
Figure 2A:
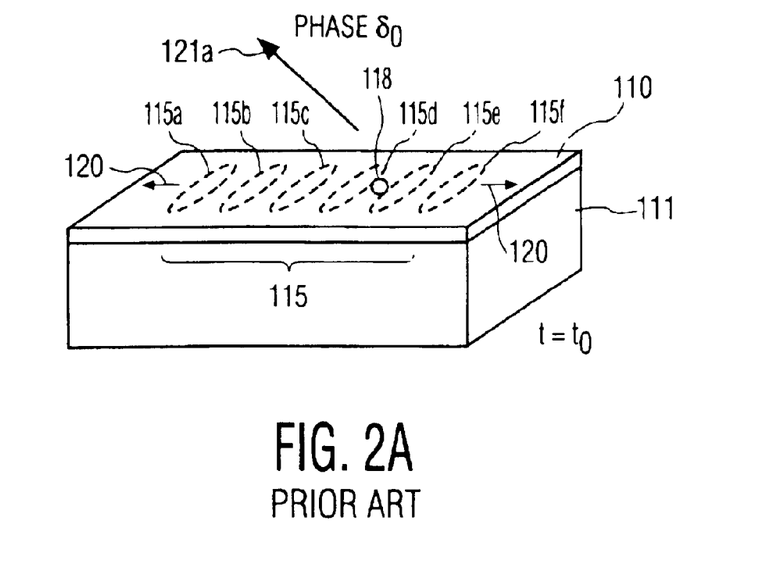
FIGS. 2A and 2B show, respectively, top views of a structure being measured in a reflection-mode geometry according to the prior art when a probe beam irradiates the structure at times $t=t_0$ and $t=t_1$.
Figure 2B:
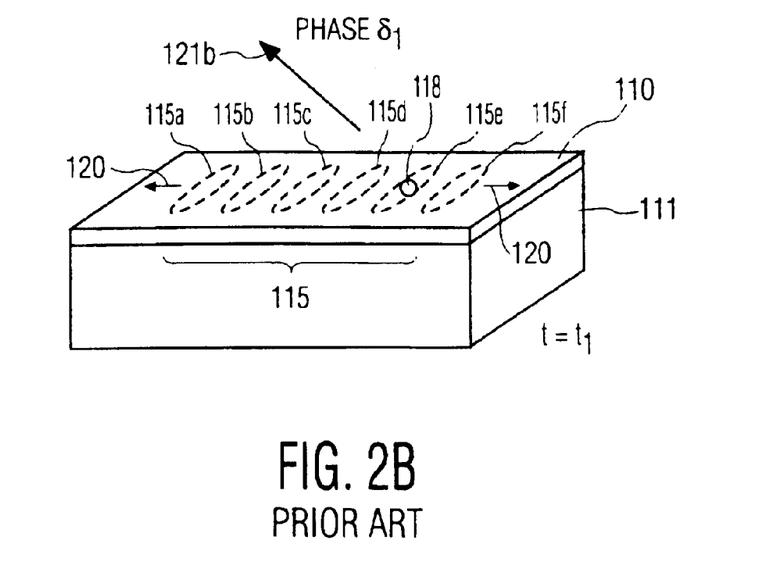

The modulated film is measured in a reflection mode geometry with a continuous probe laser beam 20 that reflects off the acoustic waves and is detected with a high-speed photodetector 80. When ripple is formed, the film's surface deflects the incident probe beam 20 to form a reflected signal beam 20', 20". The signal beam 20', 20" leaves the film 10 at an angle $\phi_n$ that depends on the oscillation cycle of surface ripple. For example, in FIG. 1C the probe beam irradiates an area 18 on a side of a ripple peak 17a and is deflected at an angle $\phi_1$ (relative to a normal vector 19) to form the signal beam 20'. FIG. 1D shows that at a later time the peak 17a undulates down, making the ripple 17 less pronounced. The probe beam now irradiates the area 18 which is relatively flat, and thus the signal beam 20" leaves the sample at an angle $\phi_2$ that is less than $\phi_1$. As the acoustic waves propagate the deflection angle oscillates continuously between $\phi_1$ and $\phi_2$ at an acoustic frequency (typically, between 200 MHz and 1 GHz). The photodector (80 in FIG. 4) detects the reflected beam to determine a data sweep. Multiple (e.g., between 50 and 500) data sweeps are averaged together and then digitized with an analog-to-digital converter in the data-acquisition electronics to form a signal waveform, similar to that shown in FIG. 9A. A computer analyzes the signal waveform as described below to measure the thickness of the film.

The accuracy and repeatability of the thickness measurement made in the reflection-mode geometry depends on how accurately and repeatably the frequency of the modulated signal beam is measured; accuracy and repeatability, in turn, depend on the signal-to-noise ratio of the signal waveform. This ratio improves as the number of averaged data sweeps increases. When the signal-to-noise ratio is 500:1 or greater, film thickness can be determined with a repeatability and accuracy that are typically less than 3 and 20 angstroms, respectively.

In the reflection-mode geometry, the signal-to-noise ratio of the signal waveform is maximized by minimizing the spatial fluctuations between the probe beam and the peaks and nulls of the ripple (or, equivalently, the light regions of the excitation pattern). For example, if there are no fluctuations between these components the measured data sweeps are in phase, and the signal waveform generated by averaging these sweeps together will have a well-defined frequency. Conversely, if spatial fluctuations between the probe area and the peaks and nulls are random and relatively large, individual data sweeps will oscillate at random phases. This "washes out" the frequency of the averaged signal waveform, making it unsuitable for thickness measurements.

FIGS. 2A–B and 3A–B illustrate this point by showing: 1) a measurement method of the prior art (FIGS. 2A–3B)

wherein the probe area 118 fluctuates relative to the light regions 115a–f of the excitation pattern 115; and 2) a measurement of the current invention (FIGS. 3A–3B) wherein the probe area 18 is fixed relative to the light regions 15a–f of the excitation pattern. In the prior art method, the phase of the light regions 115a–f fluctuates as indicated by the arrows 120 along a plane of a film 110 disposed on a substrate 111. When a data sweep is measured at time t=t$_0$, the probe area 118 is located between light regions 115d and 115e. Because of the fluctuations, at a later time t=t$_0$, the probe area is located directly on top of light region 115d. Thus, the data sweep measured at time t=t$_0$ (indicated by the arrow 121a) has a phase of $\delta_0$, while the data sweep measured at time t=t$_1$ (indicated by the arrow 121b) has a different phase of $\delta_1$. Oscillations in the resulting signal waveform are washed out when many data sweeps like these are averaged together; the resulting signal waveform looks similar to the waveform 202 shown in FIG. 9B. No well-defined frequency is present in these data, and thus the thickness of the film 110 can not be accurately measured.

Figure 3A:
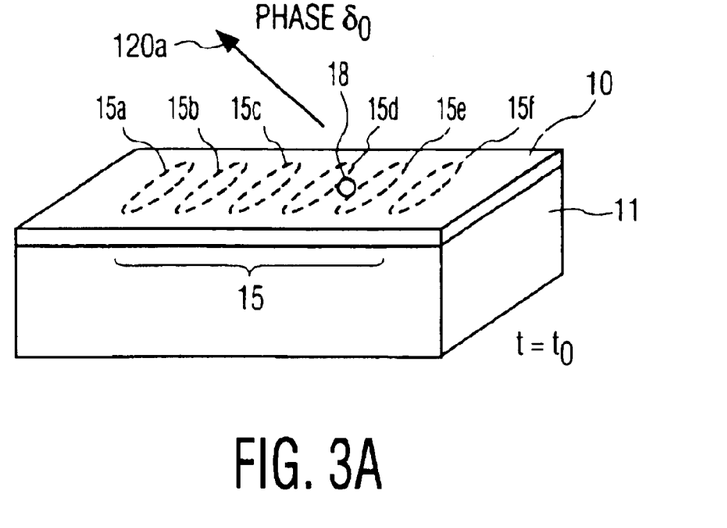
FIGS. 3A and 3B show, respectively, top views of a structure being measured in a reflection-mode geometry according to the invention when a probe beam irradiates the structure at times $t=t_0$ and $t=t_1$.
Figure 3B:
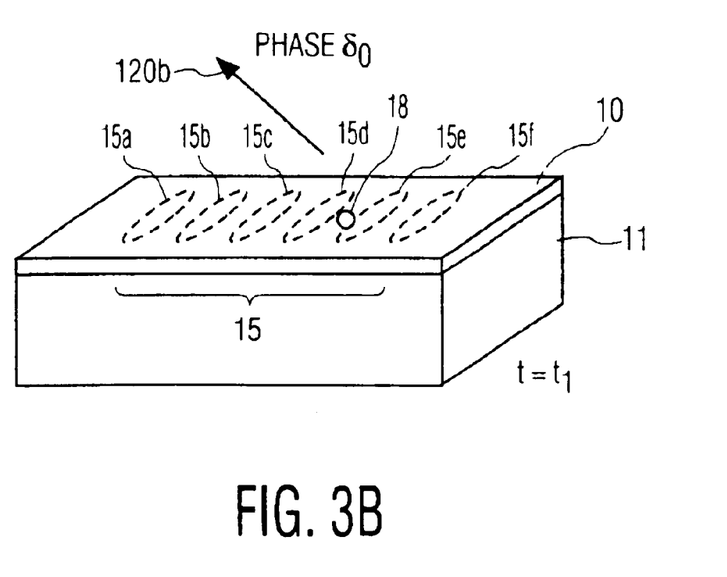

FIGS. 3A–B show that in the current invention the light regions 15a–f of the excitation pattern 15 do not fluctuate. Thus, at times t=t$_0$, t$_1$ the probe area 18 is fixed relative to the light regions 115a–f, and the data sweeps (indicated by arrows 120a, b) measured at these times have the same phase $\delta_0$. The signal waveform formed by averaging together multiple data sweeps like these looks like the waveform 200 shown in FIG. 9A, i.e. it is characterized by a well-defined frequency. From these data the thickness of the film 10 is accurately measured.

Referring again to FIG. 4, the optical system 50 measures film thickness in a reflection-mode geometry by initiating and measuring acoustic modes in a thin film 10 disposed on a substrate 10. Accurate measurements are made by fixing the phase of the excitation pattern 15 relative to the probing area 18 so that spatial sitter between these components is minimized. In particular, jitter in the phase of the excitation pattern is minimized by: 1) using a small-scale microchip laser 52 that undergoes little or no Pointing instabilities to excite acoustic modes in the film; and 2) imaging a pattern 66 from a phase mask 62 onto the film's surface to form the excitation pattern 15. Reflection-mode measurements made in this way are accurate (typically to within 20A), repeatable (typically less than 3A), rapid (less than 2 seconds/point), and can be made over a small area (as low as a few microns).

Figure 9A:
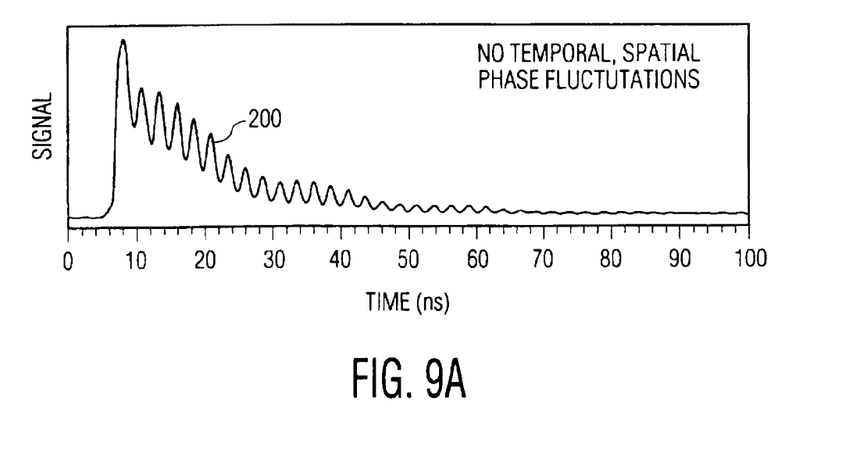
FIGS. 9A and 9B are signal waveforms measured, respectively, when no temporal and/or spatial fluctuations are present in the excitation pattern, and when temporal and/or spatial fluctuations are present in the excitation pattern.

In the system 50 the microchip laser 52 initiates time-dependent acoustic phonons in the thin film 10, and a second "probe" laser 54 measures the response to generate a signal waveform (similar to that shown in FIG. 9A). The waveform is detected with a high-speed photodetector 80 and then analyzed to determine the property of interest.

The microchip laser 52 generates a pulse 12 featuring a laser pulse 10 that has a duration of about 500 ps, an energy of about 2 microJoules, and a wavelength of 532 nm. Specifically, the laser 52 is typically a passively Q-switched Nd:YAG/Cr$^{+4}$:YAG microchip laser, such as that described in U.S. Pat. No. 5,394,413, incorporated herein by reference. During operation, the pulse 12 partially reflects (about 5%) off a glass plate 65 into a low-speed photodetector 67. The photodetector 67, in response, generates a light-induced trigger pulse (described in more detail below) that is sent to the data-acquisition electronics and used to measure the signal waveform. The remainder of the beam passes through a collimating lens 50 and a cylindrical lens 64 that focuses it onto the pattern 66 of a diffracting phase mask 62. The mask 62 is made of an optically transparent substrate (e.g., quartz or fused silica) and the pattern 66 includes a series of parallel trenches etched to have a period of between 0.1 and 100 microns and a depth d that maximizes diffraction of the incident optical wavelength (d $\sim\lambda/4$). The pattern separates the pulse from the microchip laser into at least two excitation laser pulses 12', 12'' that leave the phase mask at an angle $\theta$ that depends on the spacing of the trenches in the pattern. The pulses 12', 12'' impinge an achromat lens pair 70 that focuses and overlaps them on the sample. There, the pulses optically interfere to form a spatially and temporally varying excitation pattern 15 in or on the surface of the film 10. The pattern contains a series of periodic, sinusoidal "light" (constructive interference) and "dark" (destructive interference) regions as described above. The length and width of the pattern 15 are typically about 500 and 40 microns, respectively.

The excitation radiation pattern 15 excites acoustic waves in the film 10 that have a wavelength and orientation corresponding to the spatial wavelength of the pattern on the phase mask. Excitation of the acoustic modes occurs via ISTS, an all-optical technique described above. The acoustic modes modulate an optical property (e.g., time-dependent change in the refractive index) and/or a physical property (e.g., a time-dependent ripple morphology) in the film or on the film's surface. The frequency of the modulation depends on the thickness, density, and sound velocity of the film.

The optical system 50 is designed so that small spatial fluctuations between the initial laser pulse 12 and the phase mask 62 do not change the phase or wavelength of the excitation pattern. For example, the achromat lens pair 70 is positioned to image the diffracting pattern 66 of the mask 62 onto the sample to form the excitation pattern 15. Imaging is typically between 0.8:1 and 1.2:1; imaging is 1:1 if the spacing of both the phase mask and sample from the center of the achromat pair is 2F, where F is the effective focal length of the achromat lens pair. The pattern 66 is additionally designed so that its area (typically 1–4 mm$^2$) is significantly larger than the area of the focused excitation pulse (typically 50×300 microns). The spacing of the trenches is uniform throughout the pattern. This ensures that during operation the same pattern is always imaged onto the same, even with small spatial fluctuations in the pulse from the microchip laser.

Figure 5:
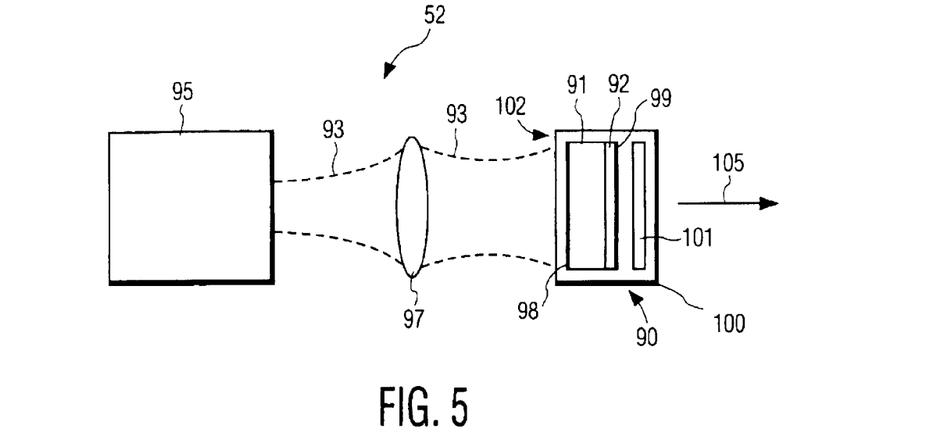
FIG. 5 shows a schematic, cross-sectional view of a microchip laser used in the optical system of FIG. 4.

Jitter in the excitation pattern is further minimized because the pulse from the microchip laser undergoes little or no Pointing fluctuations. Without being bound to any theory, the stability of the pulse appears to be due to the laser's compact geometry. FIG. 5 shows a cross section of a typical microchip laser 52 similar to that described in U.S. Pat. No. 5,394,413. The microchip 90 in the laser 52 features a gain layer 91 (typically 1.5 mm×1.5 mm×0.1–1.5 mm thick) of a Nd:YAG diffusion-bonded to a thin Cr$_{+4}$:YAG Saturable absorber 92 (typically 0.5 mm×1.5 mm ×1.0–1.5 mm thick). The entire microchip 90 is irradiated by a pump beam 93 from a diode laser 95. The pump beam 93 that has a wavelength of 803.5 nm that is chosen to be strongly absorbed by the Nd:YAG and a power of about 1.2 W. The diode laser 95 is typically modulated so that the microchip laser emits 90 a pulse at a well-defined frequency (typically 300–500 Hz). Prior to irradiating the microchip 90, the beam 93 from the diode laser 95 passes through a lens 97 (e.g., a (,GRIN lens) that focuses it onto the exposed face of the gain layer 91. The gain layer 91 contains a coating 98 that is transparent (T>90%) at 808.5 nm and highly reflective (R>99%) at 1064 nm, the fundamental emitting frequency of the Nd:YAG layer. The saturable absorber layer 92 contains a coating 99 that is partially reflective (~85%) at 1064 nm. The entire microchip 90 is contained in a metal housing 100 that additionally includes a nonlinear optical crystal 101 (typically potassium triphosphate, or KTP) that doubles the fundamental wavelength of the microchip laser (1064 nm) to 532 nm. The properties of the pulse emitted from he housing 101, indicated by the arrow 105, are described in Table 1, below:

TABLE 1

Microchip Laser Properties

| | |
|---|---|
| wavelength: | 532 nm |
| pulse energy: | 2–4 microJoules |
| pulse duration: | 500 ps |
| repetition rate: | 300–500 Hz |
| pulse-to-pulse jitter: | 0.1–50 microseconds |

Because of its small size, the microchip laser 90 is heated uniformly during the pumping process and requires only convection (i.e., air) cooling. For example, FIG. 5 shows how the pump beam 93 leaving the diode laser 95 irradiates the lens 97 and is focused to an area (about 1 mm$^2$) that is comparable to the area on the exposed surface 102 of the microchip 90. The pump beam 93 evenly heats the microchip and minimizes any thermal gradient that can lead to thermal lensing and Pointing instabilities. The resulting pulse therefore has basically no spatial jitter. As described above, this further reduces any fluctuations between the pulse and the phase mask, thereby additionally increasing the spatial stability of the excitation pattern and reducing fluctuations that can reduce the quality of data measured in the reflection-mode experiments Although the excitation pattern generated by the microchip laser lacks spatial jitter, the optical pulses generated by this light source suffer from a temporal jitter that varies from one pulse to the next. Temporal jitter occurs, for example, if the time required for gain to build up in the microchip laser cavity varies with time: it is nearly always present in passively Q-switched lasers, like the microchip laser. Temporal jitter affects the time when the laser pulse is emitted, and must be accounted for in order to accurately measure acoustic frequencies from the time-dependent signal waveforms.

To account for temporal jitter in the microchip laser pulse, the optical system in FIG. 4 includes a glass plate 65 that reflects a small portion (e.g., 5%) of the pulse 12 onto a low-speed photodetector 67 to generate a light-induced electronic trigger pulse. Once generated, the trigger pulse is sent to the data-acquisition system and used to trigger an analog-to-digital converter and/or phase-sensitive amplifier that digitizes the signal waveform for analysis. This trigger pulse is perfectly in phase with the optical pulse, and accounts for temporal jitter that is typically present in passively Q-switched lasers.

Figure 6:
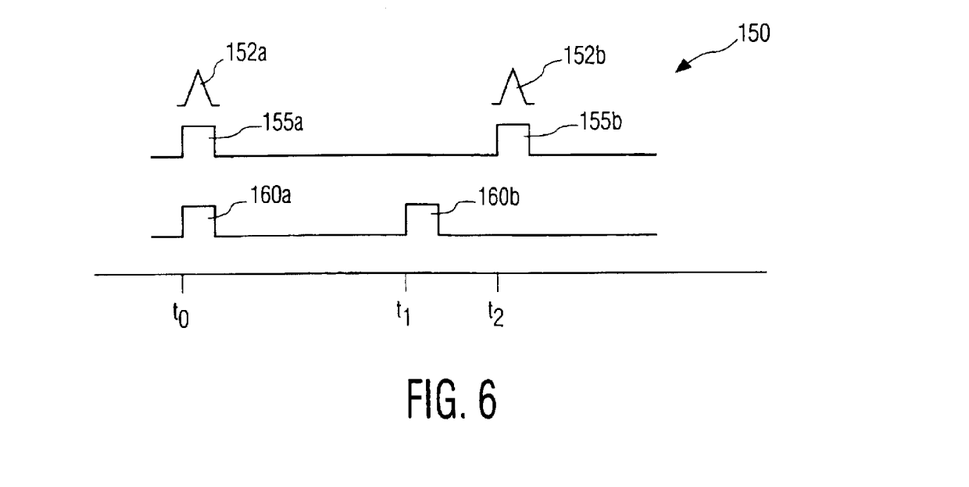
FIG. 6 shows a schematic, time-dependent profile of laser and trigger pulses generated by the microchip laser.
Figure 9B:
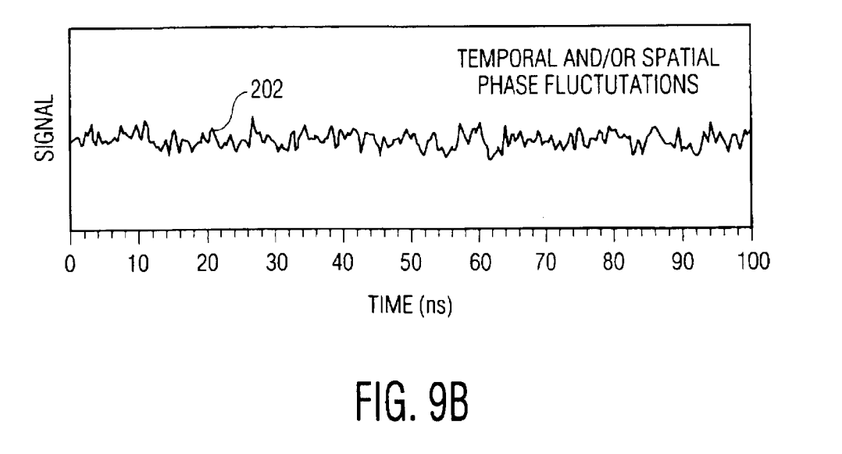

FIG. 6 shows, for example, a schematic time-dependent profile 150 of laser pulses 152a, 152b generated at times t=$t_0$, $t_2$, and the corresponding light-induced, trigger pulses 155a, 155b generated by the photodiode 67 in FIG. 6. Trigger pulses 155a and 155b and laser pulses 152a and 152b are in phase and both occur, respectively, at times t=$t_1$, $t_2$. Trigger pulses 155a, 155b can therefore be sent to the data-acquisition electronics and used as a trigger to generate signal waveforms. FIG. 9A shows, for example, a signal waveform 200 generated using this pulse as a trigger. An acoustic frequency measured from this waveform has a repeatability of about 0.01 MHz, corresponding to a thickness repeatability of about 3A. To show the affects of temporal jitter, FIG. 6 also shows pulses 160a, 160b representing time intervals when radiation from the modulated diode laser is sent to pump the microchip laser. Due to temporal jitter, the laser pulse 152b emitted from the microchip laser at time t=$t_2$ is not concurrent with the pulse 160b from the diode laser at time t=$t_2$. This pulse, therefore, could not be used as a trigger for the data-acquisition electronics. FIG. 9B shows a signal waveform 202 generated when the pulse from the diode laser is used to trigger the data-acquisition electronics. The waveform 202 clearly lacks any well-defined frequency, and can not be measured from these data.

Referring again to FIG. 4, a probe laser 54 measures acoustic waves initiated with the optical system 50 by generating a probe beam 20 that is collimated by a first lens 55 and focused with a second lens 71 to an area 18. The beam 20 features a pulse that is relatively long (typically several hundred nanoseconds or longer), and has a wavelength that is not strongly absorbed by the film (typically 830–870 nm) and is reflected off the film's surface. The probe laser beam is typically emitted from a small-scale laser diode and, like the excitation pattern, undergoes little or no spatial fluctuations. After focusing, the area 18 lies completely, within the excitation field. For example, the probe beam is focused on a peak, null, or between a peak and a null in the excitation pattern. Thus, the relative position between the excitation pattern and the probe area remains fixed.

The probe beam 20 reflects off acoustic waves generated by the excitation pattern 15, and is collected by a lens 76 that focuses it onto the high-speed detector 80 that generates a light-induced electronic signal. The signal is then analyzed with the data-acquisition electronics to generate signal waveform. The data-acquisition electronics, for example, may include a phase-sensitive amplifier, such as a lock-in amplifier, to detect the modulated component of the signal beam to generate a signal waveform. A computer (not shown in the figure) analyzes the signal waveform and computes a Fourier transform to determine an acoustic frequency or phase velocity. Film thickness is determined by processing the frequency (or phase velocity) along with the wavelength of the excitation pattern and the film's density and sound velocities as described in the above-referenced patents and applications.

Figure 7:
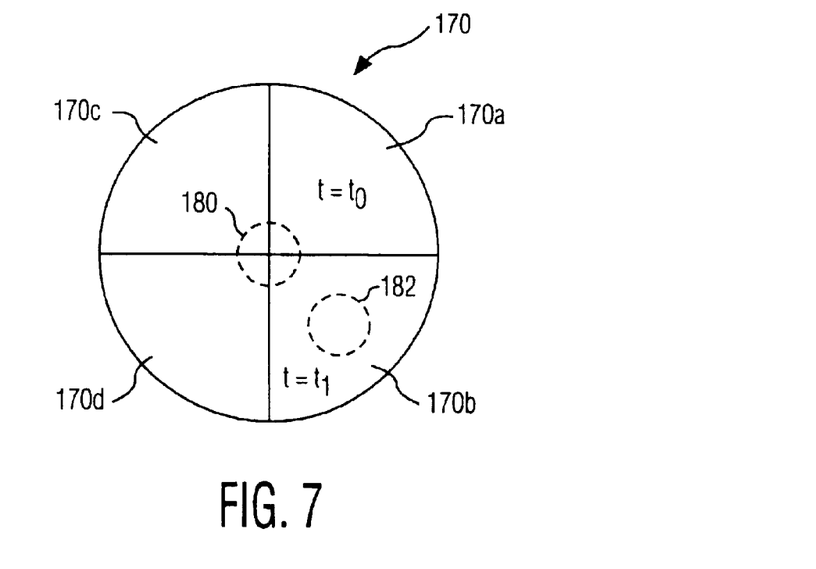
FIG. 7 shows a schematic, cross-sectional view of a bi-cell detector for detecting a reflected signal beam in the optical system of FIG. 4.
Figure 8:
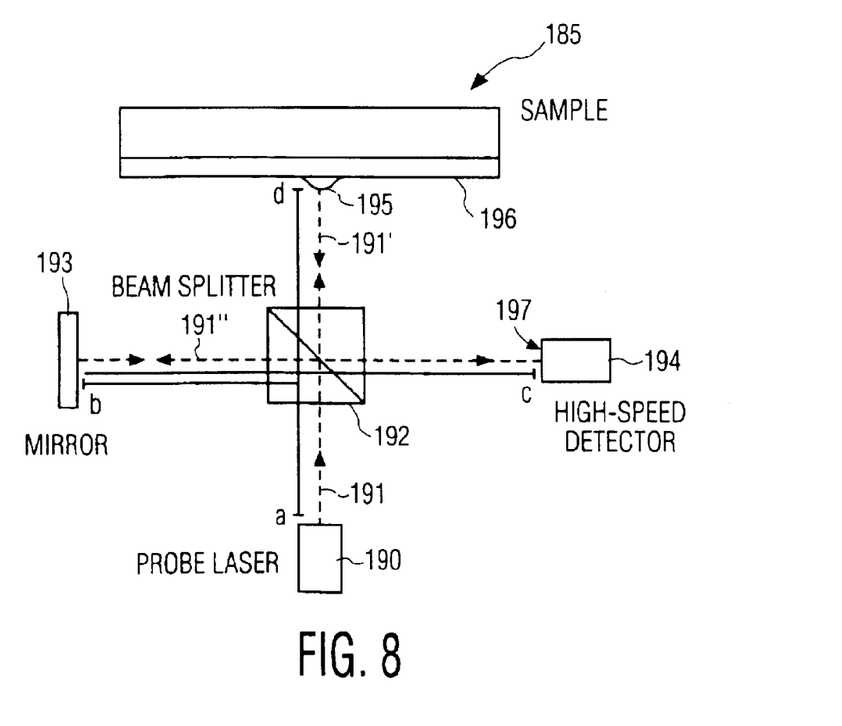
FIG. 8 shows a schematic, cross-sectional view of a interferometer detector for detecting a reflected signal beam in the optical system of FIG. 4.

FIGS. 7 and 8 show systems for detecting the reflected probe beam that can be incorporated into the optical system 50 of FIG. 4 to determine the acoustic frequency. Referring first to FIG. 7, a multiple-cell detector 170 features four different cells 170a–d, each of which generates a light-induced electrical signal having a magnitude that depends on thee power of the irradiating probe beam. The detector 170 measures a deflected probe beam modulated in a time-dependent manner by the undulating ripple morphology formed on the film surface by the ISTS-initiated acoustic waves. For example, at time t=$t_1$ the reflected probe beam is deflected by an angle $\phi_0$, and irradiates an area 180 that overlaps each of the four cells 170a–d. The ripple undulates at the acoustic frequency, and thus at a later time t=$t_1$ deflects the probe beam at a different angle $\phi_1$. The probe beam then irradiates an area 182 within a single cell 170b in the detector, thus changing the magnitude of the light-induced electrical signal generated by each of the cells. A computer (not shown in the figure) analyzes the differences in the electrical signals to determine the acoustic frequency.

FIG. 8 shows another detection system 185 that measures the frequency of the acoustic waves. The system 185 uses optical interferometry to detect phase shifts in the probe beam caused by the acoustic waves, and is described in more detail in "Real-time detection of laser-induced transient gratings and surface acoustic wave pulses with a Michelson interferometer", by T Yao-chun, et al., J. Appl. Physics, 82(10) 15 Nov. 1997, pp. 4758-62 the contents of which are incorporated herein by reference. In the detection system 185, a probe laser 190 generates a beam 191 that passes through a beamsplitter 192 that transmits about 50% of the beam 191' and reflects the remainder of the beam 191" onto a mirror 193 (i.e., along pathlength ab). The mirror 193 reflects the beam back through the beamsplitter and onto the photodetector 194 (i.e., pathlength bc). The transmitted portion 191' of the beam irradiates an undulating portion 195 of the outer surface of the film 196 (pathlength ad). This portion 195 reflects the beam back onto the partially reflecting mirror 192, which then reflects the beam into a photodetector 10 (pathlength dc). In this configuration, the beams propagating along paths ab/bc and ad/dc interfere on a light-sensitive region 197 of the detector. As indicated by arrows 10 and 10, optical pathlengths ab/bc, and ad/dc are equivalent prior to exciting acoustic phonons with ISTS. Once the phonors are excited, the undulating ripple modulates pathlength ad/dc by a distance equal to the ripple amplitude (typically a few angstroms) at the acoustic frequency. This modulation changes the phase of the beam that propagates along pathlength ad/dc relative to that propagating along pathlength ab/bc, thus changing the interference (e.g., from constructive to destructive interference) at the light-sensitive region 197 of the detector 194. This, in turn, modulates the light-induced electrical signal generated by the detector. A computer (not shown in the figure) detects the light-induced electrical response to measure the acoustic frequency.

Once detected, the frequency is analyzed according to methods described in U.S. Pat. Nos. 5,633,711, 5,546,811, and 5,672,830, described above, and U.S. Ser. No. 08/783, 486, entitled METHOD AND DEVICE FOR MEASURING THE THICKNESS OF OPAQUE AND TRANSPARENT FILMS, the contents of which have already been incorporated herein by reference.

Other Embodiments

Other embodiments are within the scope of the invention described above. In particular, optical systems other than that shown in FIG. 4 that use a phase mask to generate an excitation field to excite acoustic waves and a reflection-mode geometry to measure the waves can be used. Such systems, for example, are described in U.S. Ser. No. 08/885, 555 (entitled IMPROVED TRANSIENT-GRATING METHOD AND APPARATUS FOR MEASURING MATERIAL PROPERTIES), the contents of which are incorporated herein by reference.

Likewise, the phase mask can be replaced with a similar diffractive optical element, such as an amplitude mask or diffraction grating or an acousto or electro-optic modulator, to form the excitation pattern. The diffractive element can include patterns that simultaneously generate more than one spatial frequency, an excitation pattern that is non-periodic, or an excitation pattern that contains light regions that are shapes other than a series of parallel lines. For example, the diffractive element may generate an excitation pattern consisting of a series of concentric circles, ellipses, or other shapes. Other acceptable patterns for diffractive masks are described in U.S. Ser. No. 08/377,310, entitled DEVICE AND METHOD FOR TIME-RESOLVED OPTICAL MEASUREMENTS, the contents of which have been previously incorporated herein by reference.

Likewise, microchip lasers other than Nd:YAG/$Cr^{+4}$:YAG lasers can be used to generate the excitation pulse. For example, the laser can be a titanium:sapphire, chromium:LISAF, ring, or fiber laser.

In other embodiments the optical system can be modified to increase the magnitude of the signal beam. For example, the signal magnitude can be increased using heterodyne amplification methods. In general, heterodyne amplification is done by spatially and temporally overlapping a phase component from an additional optical beam called the heterodyne beam) with a phase component from the signal beam in a light-sensitive region of the photodetector. This process increases the amplitude of the signal measured at the detector, thereby enhancing the precision and accuracy of the thickness measurement.

In other embodiments, a portion of the probe beam is diffracted and measured along with the reflected probe beam. Measurement of diffracted beams is described in detail in U.S. Pat. Nos. 5,633,711, 5,546,811, and 5,672,830, described above.

In still other embodiments the frequency of the signal waveform can be analyzed to determine properties of the sample other than thickness. For example, the frequency can be analyzed to determine adhesion, density, stiffness, elasticity, surface roughness, and other mechanical or physical properties of a thin film. In addition, portions of the signal waveform other than frequency can be analyzed to determine other properties about the sample. For example, the shape of the waveform can be analyzed to determine the degree of adhesion, surface roughness, or composition of one or more of the films in the structure. Other properties chat can be measured from the waveform include properties of ion-implanted silicon wafers, such as the concentration and energy of the implanted ion. Measurement of these properties are described, for example, in U.S. Ser. No. 08/885,786 (entitled METHOD AND APPARATUS FOR MEASURING THE CONCENTRATION OF IONS IMPLANTED IN SEMICONDUCTOR MATERIALS) and U.S. Ser. No. 08/926,850 (entitled IMPROVED METHOD AND APPARATUS FOR MEASURING THE CONCENTRATION OF IONS IMPLANTED IN SEMICONDUCTOR MATERIALS), the contents of which are incorporated herein by reference.

The method and apparatus of the invention can be used to measure of variety of structures. For example, the method is particularly effective in determining the thickness of metal films used in the microelectronic industry. Such metal films include aluminum, copper, tungsten, titanium, tantalum, titanium:nitride, tantalum:nitride, gold, platinum, niobium, and alloys thereof. These metals may be included in single-layer and multilayer structures. Other materials that can be measured include polymers, diamond-like coatings, and buried transparent films.

Also, even though we have discussed embodiments which launch an acoustic response to measure a property of a structure, the invention also covers the launching of thermal and/or electronic responses as other ways of measuring a property of the structure. By thermal response, we mean any light-induced temperature increase induced in the structure and by electronic response we mean any light-induced response in the structure in which electrons, holes, electron-hole pairs, charge carriers, electrical charges, or ions are generated and/or initiated.

Still other embodiments are within the scope of the following claims.

What is claimed is:

1. An apparatus for measuring a property of a structure, comprising:

a microchip laser that generates an optical pulse;

a diffractive element that receives the optical pulse and diffracts it to generate at least two excitation pulses;

an optical system that receives at least two optical pulses and spatially and temporally overlaps them on or in the structure to form an excitation pattern that launches an acoustic wave, electronic response, or thermal response that modulates at least a portion of the structure;

a light source that produces a probe beam that reflects off the portion of the structure to generate a signal beam;

an optical detection system that receives the signal beam and in response generates a light-induced electrical signal; and an analyzer that analyzes the light-induced electrical signal to measure the property of the structure.

2. The apparatus of claim 1, wherein the diffractive element is a mask that comprises an optically transparent substrate that comprises a pattern comprising a series of parallel trenches having a spatial periodicity of between 0.1 and 100 microns.

3. The apparatus of claim 2, wherein the mask is a phase mask.

4. The apparatus of claim 3, wherein the phase mask comprises a plurality of patterns.

5. The apparatus of claim 1, wherein the laser is a diode-pumped laser.

6. The apparatus of claim 5, wherein the laser is a passively Q-switched laser.

7. The apparatus of claim 6, wherein the laser comprises Nd:YAG, titanium:sapphire, chromium:LISAF, or a fiber laser.

8. The apparatus of claim 7, wherein the Nd:YAG is comprised by a layer having a thickness of less than 5 mm.

9. The apparatus of claim 1, wherein the portion of the structure is a surface.

10. The apparatus of claim 9, wherein the acoustic wave generates a time-dependent ripple on the surface.

11. The apparatus of claim 10, wherein the probe beam is aligned to deflect off the time-dependent ripple to form the signal beam.

12. The apparatus of claim 11, wherein the optical detection system comprises a detector that generates an electrical signal that changes when a deflection angle of the probe beam changes.

13. The apparatus of claim 12, wherein the optical detection system comprises a detector that comprises a single photodiode.

14. The apparatus of claim 13, wherein the detector comprises at least two photodiodes.

15. The apparatus of claim 1, wherein the modulated optical, mechanical, or physical property is a temperature.

16. The apparatus of claim 11, wherein an optical, mechanical, or physical property is modulated in the portion by the acoustic waves.

17. The apparatus of claim 16, wherein a refractive index or absorption coefficient is modulated.

18. The apparatus of claim 16, wherein the probe beam is aligned to reflect off the area comprising the modulated absorption coefficient or refractive index.

19. The apparatus of claim 18, wherein the optical detection system is configured to detect a phase of the signal beam.

20. The apparatus of claim 19, wherein the optical detection system comprises an interferometer.

21. The apparatus of claim 1, wherein the optical system comprises at least one lens that collects and overlaps the excitation pulses on or in the structure.

22. The apparatus of claim 21, wherein the optical system comprises a lens pair having a magnification ratio of about 1:1.

23. The apparatus of claim 1, further comprising a lens that focuses the probe laser beam onto the portion.

24. The apparatus of claim 23, wherein the acoustic waves generate a time-dependent ripple morphology in the portion, and the probe beam irradiates a peak, null, a region between a peak or null, or a portion thereof in the ripple morphology.

25. The apparatus of claim 23, wherein the portion undergoes a time-dependent change in refractive index or absorption coefficient.

26. The apparatus of claim 1, wherein the analyzer is configured to determine a frequency or phase velocity of the acoustic waves.

27. The apparatus of claim 26, wherein the structure comprises at least one layer.

28. The apparatus of claim 27, wherein the analyzer is configured to analyze the frequency or phase velocity to determine a thickness of the layer.

29. The apparatus of claim 28, wherein the analyzer is configured to calculate a thickness of the layer by analyzing the frequency or phase velocity, a density of the layer, and a wavelength of the excitation pattern.

30. The apparatus of claim 28, wherein the structure comprises a plurality of layers, and the analyzer is configured to analyze the light-induced electrical signal to determine the thickness of more than one layer in the structure.

31. The apparatus of claim 27, wherein the analyzer is configured to determine the density, resistivity, adhesion, delamination, elasticity, toughness, or reflectivity of the structure or the layer in the structure.

32. The apparatus of claim 27, wherein the structure comprises a semiconductor.

33. The apparatus of claim 32, wherein the layer is a metal film.

34. The apparatus of claim 33, wherein the metal comprises aluminum, tungsten, copper, titanium, tantalum, titanium:nitride, tantalum:nitride, gold, silver, platinum, or alloys thereof.

35. A method for measuring a property of a structure, comprising the steps of:

generating an optical excitation pulse with a diode-pumped microchip laser;

diffracting the optical pulses with a diffracting element to generate at least two excitation pulses;

spatially and temporally overlapping the excitation pulses on or in the structure to form an excitation pattern that launches an acoustic wave, an electronic response, or a thermal response that modulates at least a portion of the structure;

reflecting a probe beam off the portion to generate a signal beam;

detecting the signal beam to generate a light-induced electrical signal; and analyzing the light-induced electrical signal to measure the property of the structure.

* * * * *